United States Patent [19]

Hayashi et al.

[11] 4,070,377

[45] Jan. 24, 1978

[54] PROCESS FOR PRODUCING L-ASCORBIC ACID-2-SULFATE

[75] Inventors: Eiichi Hayashi, Shizuoka; Kiyoshi Takita, Shimizu; Hironari Sugiyama, Shimizu; Yukio Nezu, Shimizu, all of Japan

[73] Assignee: Kumiai Chemical Industry Co., Ltd., Tokyo, Japan

[21] Appl. No.: 711,409

[22] Filed: Aug. 3, 1976

Related U.S. Application Data

[63] Continuation-in-part of Ser. No. 521,767, Nov. 7, 1974, abandoned.

[30] Foreign Application Priority Data

Nov. 7, 1973 Japan .............................. 48-124395
Nov. 8, 1973 Japan .............................. 48-124951

[51] Int. Cl.$^2$ ............................................ C07D 307/32
[52] U.S. Cl. ................................................... 260/343.7
[58] Field of Search ...................................... 260/343.7

[56] References Cited

FOREIGN PATENT DOCUMENTS 7,430,354  3/1974  Japan .............................. 260/343.7

OTHER PUBLICATIONS

Gilbert, Sulfonation & Related Reactions (Interscience, 1965), p. 374.
Quadri, Diss. Abstr. Int. B, Mar. 1974, 34(9), 4431–4432.
Quadri, et al., Carbohyd. Res. 1973, 29(1), 259–264.

Primary Examiner—Cecilia M. S. Jaisle
Attorney, Agent, or Firm—Oblon, Fisher, Spivak, McClelland & Maier

[57] ABSTRACT

A process for producing a mono- or di-alkali metal salt or alkaline earth metal salt of L-ascorbic acid-2-sulfate which comprises reacting L-ascorbic acid in which the 5 and 6 positions are protected by a ketone or aldehyde, with dimethyl formamide-sulfur trioxide complex, and neutralizing the product with an alkali metal hydroxide or an alkaline earth metal hydroxide, and removing said protecting aldehyde or ketone at 5-and 6-positions.

7 Claims, No Drawings

PROCESS FOR PRODUCING L-ASCORBIC ACID-2-SULFATE

REFERENCE TO RELATED APPLICATION

This application is a continuation-in-part of Ser. No. 521,767, filed Nov. 7, 1974, and now abandoned.

BACKGROUND OF THE INVENTION

1. Field of the Invention

The present invention relates to a process for economically producing L-ascorbic acid-2-sulfate and salts thereof of high purity in high yield. These compounds are useful as medicines, domestic medicines, animal medicines and as additives for food, feed and cosmetic materials.

2. Description of the Prior Art

The synthesis of salts of L-ascorbic acid-sulfate has been demonstrated by reaction of pyridine-sulfur trioxide complex with 5,6-O-benzylidene-L-ascorbic acid and then converting the product to the potassium salt thereof. [T. M. Chu et al. Steroids 1968, 12, (3) 309–321; S. F. Quadri, Diss Abstr. Int.B, Vol 34 (9) 4431 – 4432 (1974); S. F. Quadri, et. al., Carbonhyd. Res. Vol. 29 (1) 259 – 264 (1973); Murata Japanese Unexamined Patent Publication No. 30354/1974 (1974)]. However, the yield from such process has been low, and high purity products could not be obtained. Accordingly, a need exists to provide a method by which L-ascorbic acid-L-sulfate and salts thereof, can be produced economically in high yields and high purity.

SUMMARY OF THE INVENTION

Accordingly, it is an object of the present invention to provide a process for producing L-ascorbic acid-2-sulfate or a salt thereof having high purity in an industrial and economical manner. The object of the present invention has been attained by reacting L-ascorbic acid, having the 5- and 6-positions protected by a ketone or aldehyde, with a dimethyl formamide-sulfur trioxide complex, neutralizing the product with an alkali metal hydroxide or an alkaline earth metal hydroxide and acidifying the product to remove the protecting substituent at the 5-and 6-positions.

DETAILED DESCRIPTION OF THE PREFERRED EMBODIMENTS

In this process, L-ascorbic acid is employed in which the 5- and 6-positions are protected by a ketone e.g. acetone, methylethyl ketone, diisopropyl ketone, cyclohexanone, and benzophenone or an aldehyde e.g. acetaldehyde, propionaldehyde, benzaldehyde, chlorobenzaldehyde or methyl benzaldehyde. The L-ascorbic acid having such protecting substituent is treated with a dimethyl formamide-sulfur trioxide complex, which is produced by reaction of a sulfating agent e.g. sulfuric anhydride, or an alkali chlorosulfonate and dimethyl formamide. The alkali metal salt of L-ascorbic acid having a protecting substituent at the 5- and 6-position can be treated with the dimethyl formamide-sulfur trioxide complex and inert solvents.

The sulfated product may be neutralized with an alkali metal hydroxide or an alkaline earth metal hydroxide to form a di-alkali salt of L-ascorbic acid sulfate having a protecting substituent at the 5- and 6-positions. The product can then be acidified with an inorganic acid e.g. sulfuric acid, hydrochloric acid or an organic acid e.g. acetic acid to remove the protecting substituent at the 5- and 6-positions and to produce mono-alkali metal salts of L-ascorbic acid-2-sulfate. If desired, 2,3-dialkali metal salts of L-ascorbic acid-2-sulfate can be produced by further reaction with an alkali metal hydroxide.

In the reaction, 1 – 2 moles of the dimethyl formamidesulfur trioxide complex to 1 mole of the L-ascorbic acid having a protecting substituent at 5- and 6-positions is used. The reaction temperature of the sulfation is in a range of $-40°$ C to $100°$ C, preferably $0°$ C to $40°$ C, and the reaction time is from 10 minutes to 20 hours. The solvating medium can be dimethyl formamide, dioxane, tetrahydrofuran, or the like. After the sulfation, the product is neutralized using an alkali metal hydroxide or an alkaline earth metal hydroxide at low temperature, to produce the alkali metal or alkaline earth metal salt of L-ascorbic acid having a protecting substituent at the 5- and 6-positions. The product is separated and heated with an inorganic or organic acid to remove the protecting substituent at 5- and 6- positions. A mono-alkali metal salt or alkaline earth metal salt of L-ascorbic acid-2-sulfate is thereby obtained. This product can be converted to the di-alkali metal salt or alkaline-earth metal salt of L-ascorbic acid-2-sulfate.

The following are the novel and important embodiments of the present invention.

1. Mono- or di-alkali metal salts or alkaline earth metal salts of L-ascorbic acid-2-sulfate are preferably produced by reacting (1) L-ascorbic acid in which the 5- and 6-positions are protected by a ketone or aldehyde, with (2) a dimethyl formamide-sulfur trioxide complex, which is produced by reaction of sulfating agent, selected from the group consisting of sulfuric anhydride, and an alkali chlorosulfonate and, (3) inert solvents, so as to produce a sulfate, and then neutralizing the product with an alkali metal hydroxide or an alkaline earth metal hydroxide, and then removing the protecting substituent at 5- and 6-positions.

2. The compound is also preferably produced by reacting L-ascorbic acid in which the 5- and 6-positions are protected by a ketone or aldehyde, with the dimethyl formamide-sulfur trioxide complex and then neutralizing this sulfate with an alkali metal hydroxide or an alkaline earth metal hydroxide followed by removing the protecting substituent at 5- and 6-positions.

The resulting products can be shown by the formula

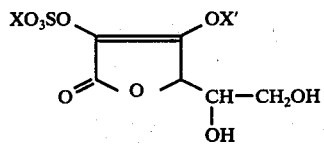

wherein X represents an alkali metal or an alkaline earth metal, and X' is hydrogen, an alkali metal or an alkaline earth metal, particularly lithium, potassium or sodium or beryllium, magnesium, calcium, barium or strontium.

In the present invention, the dimethyl formamide-sulfur trioxide complex is used as a sulfating agent whereby excellent result can be attained. However, when the other sulfating agents are used instead of the dimethyl formamide-sulfur trioxide complex, inferior results were found as follows.

| Sulfating agent | Result |
| --- | --- |
| Sulfuric anhydride | Large amount of decomposed material is formed and the product can not be separated by crystallization. Yield 5 to 10% |
| Chlorosulfonic acid | " Yield 5 to 10% |
| Sulfuryl chloride | " Yield 10 to 20% |

Having generally described the invention, a more complete understanding can be obtained by reference to certain specific examples, which are included for purposes of illustration only and are not intended to be limiting unless otherwise specified.

EXAMPLE 1

To a solution of 21.6 g of 5,6-O-isopropylidene-L-ascorbic acid in 150 ml of dimethylformamide was added dropwise 137 ml of a solution of 48 g sulfuric anhydride in 700 ml of dimethylformamide, the reaction solution being kept at 0°–10° C during this addition. The mixture was stirred at room temperature for 3 hours after the addition, and 2N KOH was added to the reaction mixture to adjust the pH to 7.0. The product was filtered and the filtrate concentrated and dissolved in water. 2N HCl was added to the solution to adjust the pH to 2.3. 24.8 g of monopotassium salt of 5,6-O-isopropylidine-L-ascorbic acid-2-sulfate was obtained. The product was dissolved in 30 ml of water and the solution was stirred at 60° C for 45 minutes, concentrated under reduced pressure and the product recrystallized from water to give 29.8 g of white needlelike crystals of the mono-potassium salt of L-ascorbic acid-2-sulfate having a decomposition point of 55°–56° C (Yield 85.6%),

| Elemental Analysis | $C_6H_7O_9SK \cdot 3H_2O$ | |
| --- | --- | --- |
| | Calculated (%) | Found (%) |
| C: | 20.69 | 20.81 |
| H: | 3.76 | 3.72 |

EXAMPLE 2

In accordance with the process of Example 1, 26.4 g of mono-potassium salt of 5,6-O-isopropylidene-L-ascorbic acid-2-sulfate was dissolved in 30 ml of water and the solution was stirred at 60° C for 45 hours and then was cooled, 2N KOH was added to the solution to adjust the pH to 7.0, and then methanol was added to the solution to crystallize it. 29.9 g of white-flake crystals of the di-potassium salt of L-ascorbic acid-2-sulfate having a decomposing point of 136°–140° C was obtained (Yield 81.2%).

| Elemental Analysis | $C_6H_6O_9SK_2 \cdot 2H_2O$ | |
| --- | --- | --- |
| | Calculated (%) | Found (%) |
| C: | 19.56 | 19.36 |
| H: | 2.74 | 2.54 |

EXAMPLE 3

43.2 g of 5,6-O-isopropylidene-L-ascorbic acid was dissolved in 300 ml of dimethyl formamide. A 274 ml of solution prepared by dissolving 48 g of sulfuric anhydride in 700 ml of dimethyl formamide was added dropwise to the solution at 0°–10° C. The mixture was then stirred at room temperature for 3 hours, and 2N NaOH was added to the reaction mixture to adjust the pH to 7.0. The product was filtered and the filtrate was concentrated, and dissolved in water. 2N HCl was added to the solution to adjust the pH to 2.3. 24.6 g of white needle-like crystals of the mono-sodium salt of 5,6-O-isopropylidine-L-ascorbic acid-2-sulfate was obtained. The product was dissolved in 60 ml of water and the solution was stirred at 60° C for 45 minutes and cooled. 2N NaOH was added to the solution to adjust the pH to 7.0, and then methanol was added and 66.0 g of white needle-like crystals of di-sodium salt of L-ascorbic acid-2-sulfate having melting point of 70°–73° C was obtained (Yield 88.7%).

| Elemental Analysis | $C_6H_6O_9SNa_2 \cdot 4H_2O$ | |
| --- | --- | --- |
| | Calculated (%) | Found (%) |
| C: | 19.36 | 19.52 |
| H: | 3.79 | 3.69 |

EXAMPLE 4

In place of 5,6-O-isopropylidene-L-ascorbic acid of Example 1, 25.6 g of 5,6-O-cyclohexylidine-L-ascorbic acid was sulfated and 2N KOH was added to the solution to adjust the pH to 7.0. The product was dissolved in water ant then 2N HCl was added to the solution to adjust the pH to 2.3, whereby 30.4 g of white crystals was obtained. The crystals were dissolved in 30 ml of water and the solution was stirred at 60° C for 2 hours and concentrated under reduced pressure. The product was recrystallized from water to give 29.0 g of white needle-like crystals of the mono-potassium salt of L-ascorbic acid-2-sulfate having a decomposition point of 55°–56° C. (Yield 83.3%)

EXAMPLE 5

In accordance with the process of Example 1, 15.8 g of 5,6-O-isopropylidene-L-ascorbic acid was used as the starting material, sulfated and a saturated solution of calcium hydroxide was added to a solution of the product to adjust the pH to 7.0. Methanol was added to the solution, whereby 34.2 g of white powdery crystals of the calcium salt of L-ascorbic acid-2-sulfate having a decomposition temperature of 70°–72° C was obtained. (Yield 87.4%).

| Elemental Analysis | $C_6H_6O_9SCa \cdot 2H_2O$ | |
| --- | --- | --- |
| | Calculated (%) | Found (%) |
| C: | 20.69 | 20.50 |
| H: | 3.47 | 3.30 |

EXAMPLE 6

18.5 g of potassium chlorosulfonate was added to 130 ml of dimethyl formamide. A solution of 21.6 g of 5,6-O-isopropylidene-L-ascorbic acid in 150 ml of dimethyl formamide was added dropwise to this solution at 0°–10° C. The mixture was then stirred at room temperature for 3 hours, and then 2N KOH was added to adjust the pH to 7.0. The product was filtered, the filtrate concentrated, and dissolved in water, and then 2N HCl was added to the solution to adjust the pH to 2.3 whereby 26.5 g of white needle-like crystals were obtained. The crystals were dissolved in 30 ml of water and the solution was stirred at 60° C for 1 hour and then concentrated. The residue was recrystallized from water to give 20.5 g of white needle-like crystals of the mono-potassium salt of L-ascorbic acid-2-sulfate having a decomposition temperature of 55°–56° C.

EXAMPLE 7

In accordance with the process of Example 6 except using sodium chlorosulfonate and the sodium salt of 5,6-O-cyclohexylidene-L-ascorbic acid instead of potassium chlorosulfonate and 5,6-O-isopropylidene-L-ascorbic acid, 15.6 g of the mono-potassium salt of L-ascorbic acid-2-sulfate having a decomposition temperature of 55°–56° C was obtained.

EXAMPLE 8

2N KOH was added to the solution of mono-potassium salt of L-ascorbic acid-2-sulfate prepared in accordance with the process of Example 6 in order to adjust the pH to 7.0. Methanol was then added to give 31.3 g of white flake crystals of the di-potassium salt of L-ascorbic acid-2-sulfate having a decomposition point of 136°–140° C.

EXAMPLE 9

Using the same starting materials and process of Examples 6 and 8 except the pH was adjusted with 2N NaOH instead of 2N KOH, 27.8 g of white needle-like crystals of the di-sodium salt of L-ascorbic acid-2-sulfate having a melting point of 70°–72° C was obtained.

REFERENCE

Preparation of dimethyl formamide-sulfur trioxide complex 8.8 g of dimethyl formamide was admixed with 100 ml of dichloroethane and 8.0 g of sulfuric anhydride was added dropwise to the mixture at 15° C to give white needle-like crystals of dimethyl formamidesulfur trioxide complex in stoichometrical amount.

EXAMPLE 10

21.6 g of 5,6-O-isopropylidene-L-ascorbic acid was dissolved in 200 ml of tetrahydrofuran. 22.9 g of dimethyl formamidesulfur trioxide complex was added to the solution at 10° C and the mixture was stirred for 30 minutes. After the reaction, the reaction mixture was neutralized with 3N-NaOH solution, and the resulting precipitate was filtered and the filtrate was concentrated under a reduced pressure to give white needle-like crystals. The crystals were dissolved in 100 ml of water and 3N-$H_2SO_4$ solution was added to the solution to adjust pH 2.0. After the pH adjustment, the solution was stirred at 60° C for 1 hour to hydrolyze the product and then 3N-NaOH solution was added to it to adjust pH 7.0. The precipitate formed by the neutralization was filtered and the filtrate was concentrated under a reduced pressure. The residue was dissolved in 20 ml of water and was recrystallized in ice-box to obtain 31.79 g of di-sodium salt of L-ascorbic acid-2-sulfate having a melting point of 70° to 73° C (Yield 85.4%).

| Elemental Analysis | $C_6H_6O_9SNa_2 \cdot 4H_2O$ | |
| --- | --- | --- |
| | Calculated (%) | Found (%) |
| C: | 19.36 | 19.48 |
| H: | 3.79 | 3.70 |

EXAMPLE 11

The residue produced by hydrolysis and post-treatment in Example 10 was dissolved in 20 ml of water at 60° C and 40 ml of methyl alcohol was gradually added dropwise to it with stirring to cool it at 5° C to give 27.67 g of white needle-like crystals of disodium salt of L-ascorbic acid-2-sulfate having a melting point of 130 to 140° C and a decomposition temperature of 185° to 190° C (Yield 82.3%).

| Elemental Analysis | $C_6H_6O_9SNa_2 \cdot 2H_2O$ | |
| --- | --- | --- |
| | Calculated (%) | Found (%) |
| C: | 21.44 | 21.21 |
| H: | 3.00 | 2.89 |

EXAMPLE 12

21.6 of 5,6-O-isoproylidene-L-ascorbic acid was dissolved in 100 ml of dimethyl formamide and 22.9 g of dimethyl formamidesulfur trioxide complex was added to the solution at 40° C and the mixture was stirred for 30 minutes. In accordance with the process of Example 10, the reaction product was treated to give 32.4 g of white needle-like crystals of di-sodium salt of L-ascorbic acid-2-sulfate having melting point of 72 to 73° C (Yield 87.2%).

| Elemental Analysis | $C_6H_6O_9SNa_2 \cdot 4H_2O$ | |
| --- | --- | --- |
| | Calculated (%) | Found (%) |
| C: | 19.36 | 19.51 |
| H: | 3.79 | 3.74 |

The compounds obtained in the present process supply sulfate groups to steroid materials, such as anticoagulants, having a heparin-like effect, antihemostat, cholesterol, etc. so as to improve their metabolism in the human and animal body. They are also biologically active in animal bodies. In fowl they have an effect on the eggs laid by the birds, causing a strengthening of the eggshells. This effect is superior to the use of the addition of Vitamin C to the fowl feeds, because Vitamin C tends to be readily decomposed, particularly in the summer months. These compounds are also useful as additives for food, feed and cosmetic materials.

The damage to eggshells during transportation is higher than 5%. It is therefore quite important from an economical viewpoint to strengthen the shells to prevent breakage.

The novel compounds of this invention are useful for the prevention of egg breakage by strengthening the shells of the eggs laid by the birds which are administered effective amounts of the results of this invention. This effect can be obtained by adding 1–100 ppm, preferably 10–50 ppm, of the compounds of this invention in feed or in drinking water of domestic fowl, especially hens. Injection of from 0.5 to 5 mg of the compound into each hen is also effective. When the compound is added to the bird's feed or drinking water, it is preferable to prepare a master batch containing the compound long with an additive such as lactose, wheat flour, talc, starch, powdery feed, an emulsifier, etc.

The following experiment was conducted to determine the effectiveness of the compounds of this invention in preventing the breaking of egg shells.

500 of hens (White leghorn), 36 weeks of age were divided into five groups of 100 hens each. Each composition of basal ration of Table 1 was admixed with 30 ppm of vitamin-C, or 30 ppm of the mono-potassium salt, the di-sodium salt or the di-calcium salt of L-ascorbic acid-2-sulfate kept at room temperature for 30 days. The compositions were then fed to each group of hens. After 30 days and 60 days from the initiation of feeding these compositions, the strength and thickness of the individual eggshells in each group of eggs were measured. The average strength and average thickness of the eggshells in each group are shown in Table 2.

Table 1

| Composition of Basal Ration | |
|---|---|
| Ingredient | % of Diet (Complete laying mash) |
| Corn | 15.00 |
| Oats | 15.00 |
| Soybean mean | 15.00 |
| Wheat | 10.00 |
| Fish meal | 7.00 |
| Tapioca flour | 6.00 |
| Corn glutten feed | 5.50 |
| $CaCO_3$ | 4.50 |
| Wheat bran | 3.25 |
| Molasses | 3.00 |
| wheat middlings | 2.75 |
| Dehydrated alfalfa mean | 2.75 |
| Mineral Mixture | 1.00 |
| | 100.00 |
| **Composition: Mineral | % |
| $CaHPO_4$ | 65.0 |
| $CaCO_3$ | 19.5 |
| Iodized salt | 13.5 |
| Trace element mixture | 2.0 |
| | 100.00 |

Table 2

| | Strength and Thickness of Eggshells | | |
|---|---|---|---|
| Additive | Item of test | After 30 days | After 60 days |
| None | strength | 3.51 kg (100%) | 3.49 kg (100%) |
| | thickness | 0.331 mm (100%) | 0.330 mm (100%) |
| 30 ppm Vitamin-C | strength | 3.54 kg (100.8%) | 3.50 kg (100.2%) |
| | thickness | 0.339 mm (102.4%) | 0.339 mm (102.7%) |
| 30 ppm mono-potassium salt of L-ascorbic acid-2-sulfate | strength | 3.86 kg (109.9%) | 3.85 kg (110.3%) |
| | thickness | 0.356 mm (107.5%) | 0.357 mm (108.0%) |
| 30 ppm di-sodium salt of L-ascorbic acid-2-sulfate | strength | 3.86 kg (109.9%) | 3.88 kg (111.2%) |
| | thickness | 0.357 mm (107.8%) | 0.358 mm (108.5%) |
| 30 ppm calcium salt of L-ascorbic acid-2-sulfate | strength | 3.88 kg (110.5%) | 3.90 kg (111.7%) |
| | thickness | 0.359 mm (108.4%) | 0.362 mm (109.7%) |

When the strength of eggshells exhibit increases of 10% over those of the standard (non-additive), the breaking of eggshells in transportation is completely eliminated. In Table 2, the percentages of the strength and thickness are based on those of the standard (non-additive)

The mono-and di-sodium salts and calcium salt of L-ascorbic acid-2-sulfate produced by the process of this invention, impart no potassium problem, as compared to known potassium salts of L-ascorbic acid-2-sulfate. They have high anti-hygroscopic and antioxidative properties and are quite stable in medicinal formulations, as well as in feed, foods and cosmetic compositions.

Having now fully described the invention, it will be apparent to one of ordinary skill in the art that many changes and modifications can be made thereto without departing from the spirit or scope of the invention as set forth herein.

What is claimed as new and desired to be secured by letters patent is:

1. A process for producing a mono- or di-alkali metal salt or alkaline earth metal salt of L-ascorbic acid-2-sulfate which consists essentially of:
    A. reacting L-ascorbic acid in which the 5- and 6- positions are protected by a ketone or aldehyde, with dimethyl formamide-sulfur trioxide complex in an inert solvent,
    B. neutralizing the product with an alkali metal hydroxide or an alkaline earth metal hydroxide, and
    C. removing said protecting aldehyde or ketone at the 5-and 6-positions.

2. A process according to claim 1 wherein the dimethyl formamide-sulfur trioxide complex is produced by a reaction of dimethyl formamide with sulfuric anhydride or alkali metal chlorosulfonate.

3. A process according to claim 1 wherein excess of dimethyl formamide is used as the inert solvent.

4. A process according to claim 1 wherein the dimethyl formamide-sulfur trioxide complex is formed by adding sulfuric anhydride or alkaki metal chlorosulfonate to a mixture of dimethyl formamide and L-ascorbic acid in which the 5- and 6-positions are protected by a ketone or aldehyde.

5. A process according to claim 1 wherein the molar ratio of the L-ascorbic acid in which the 5- and 6-positions are protected by a ketone or aldehyde to the dimethyl formamide-sulfur trioxide complex in the reaction is in the range of 1 : 1 to 2.

6. A process according to claim 1 wherein the reaction temperature in the sulfating reaction is in the range of $-40°$ C to $100°$ C.

7. A process according to claim 1 wherein the inert solvent is dimethyl formamide, dioxane, or tetrahydrofuran.

* * * * *